(12) United States Patent
Han et al.

(10) Patent No.: US 10,429,293 B2
(45) Date of Patent: Oct. 1, 2019

(54) CELL ANALYSIS APPARATUS USING PLURALITY OF LASERS

(71) Applicant: THE CATHOLIC UNIVERSITY OF KOREA INDUSTRY-ACADEMIC COOPERATION FOUNDATION, Seoul (KR)

(72) Inventors: Kyung Ja Han, Gwacheon-si (KR); Won Lee, Gwacheon-si (KR)

(73) Assignee: The Catholic University of Korea Industry—Academic Cooperation Foundation (KR)

( * ) Notice: Subject to any disclaimer, the term of this patent is extended or adjusted under 35 U.S.C. 154(b) by 0 days.

(21) Appl. No.: 15/541,287

(22) PCT Filed: Oct. 28, 2015

(86) PCT No.: PCT/KR2015/011417
§ 371 (c)(1),
(2) Date: Jun. 30, 2017

(87) PCT Pub. No.: WO2017/022885
PCT Pub. Date: Feb. 9, 2017

(65) Prior Publication Data
US 2017/0363532 A1 Dec. 21, 2017

(30) Foreign Application Priority Data

Jul. 31, 2015 (KR) .................. 10-2015-0109036

(51) Int. Cl.
*G01N 15/14* (2006.01)
*C12M 1/34* (2006.01)
(Continued)

(52) U.S. Cl.
CPC .......... *G01N 15/1429* (2013.01); *C12M 1/34* (2013.01); *G01N 15/1434* (2013.01);
(Continued)

(58) Field of Classification Search
None
See application file for complete search history.

(56) References Cited

U.S. PATENT DOCUMENTS

| | | |
|---|---|---|
| 5,041,733 A | 8/1991 | Noguchi et al. |
| 7,990,525 B2 | 8/2011 | Kanda |

(Continued)

FOREIGN PATENT DOCUMENTS

| | | |
|---|---|---|
| CN | 101206308 A | 6/2008 |
| EP | 2784481 A2 | 10/2014 |

(Continued)

OTHER PUBLICATIONS

International Search Report (in English and Korean) and Written Opinion (in Korean) of the International Searching Authority issued in PCT/KR2015/011417, dated Apr. 27, 2016, ISA/KR.

*Primary Examiner* — Neil N Turk
(74) *Attorney, Agent, or Firm* — Harness, Dickey & Pierce, PLC

(57) ABSTRACT

Provided is a light scattering cell classification technology which can classify cells into various types and at the same time classify cells with very high accuracy despite the rotation of the cells. A cell analysis apparatus using a plurality of lasers, according to an embodiment of the present invention, comprises: a plurality of laser generators which are installed around a movement path through which cells to be classified are moved, and which irradiate laser beams at one measurement point on the movement path at different angles; a plurality of photodetectors, installed around the one measurement point, which collect a second laser beam, which is a laser beam generated as the laser beams irradiated from the laser generators are incident on the cells and then scattered; and a cell analysis unit which (Continued)

classifies the cells to be classified according to the second laser beam collected by the photodetectors.

5 Claims, 5 Drawing Sheets

(51) Int. Cl.
    *G01N 21/47*     (2006.01)
    *G01N 15/02*     (2006.01)
    *G01N 15/10*     (2006.01)

(52) U.S. Cl.
    CPC ..... *G01N 15/1459* (2013.01); *G01N 21/4795* (2013.01); *G01N 15/0227* (2013.01); *G01N 2015/1006* (2013.01); *G01N 2015/1477* (2013.01)

(56) References Cited

U.S. PATENT DOCUMENTS

| | | | |
|---|---|---|---|
| 8,405,048 | B2 | 3/2013 | Hayashi |
| 2003/0026468 | A1* | 2/2003 | Chu ............... G01N 15/147 382/131 |
| 2009/0122311 | A1 | 5/2009 | Kanda |

FOREIGN PATENT DOCUMENTS

| | | |
|---|---|---|
| JP | H05-060751 A | 3/1993 |
| JP | H09-96603 A | 4/1997 |
| JP | 2006-010630 A | 1/2006 |
| JP | 2007-046947 A | 2/2007 |
| KR | 10-2010-0110369 A | 10/2010 |
| KR | 10-2012-0041870 A | 5/2012 |
| WO | WO 2010/021627 A1 | 2/2010 |

* cited by examiner

CELL ANALYSIS APPARATUS USING PLURALITY OF LASERS

TECHNICAL FIELD

The present invention relates to a technique for classifying cells by irradiating multiple laser beams for classification of target cells and then analyzing the laser beam scattered by the cells, and more particularly, to a technique for minimizing reduction in classification accuracy due to the movement of the cells and the like, thereby enabling more detailed cell classification.

BACKGROUND ART

In flow cytometry, white blood cell (WBC) differential count, or the like, various cells, such as white blood cells, are classified in order to classify normal cells and abnormal cells. These tests have been used to test various diseases, and the accuracy thereof, i.e. correctly classifying different types of cells, is very important.

Korean Patent Laid-Open Publication No. 2005-094097 discloses a method for classifying cells, which includes: irradiating the cells using a laser beam source, such as a laser diode; collecting a distribution of scattered light according to a light scattering effect caused by the components of the cells, such as the nuclei, as the light passes through the cells; and classifying the cells based on the collected scattered light.

The above-described conventional technique classifies the types of cells by irradiating a single laser beam, providing a plurality of photodetectors at a portion to which the irradiated laser beam is directed through the cells, and measuring light density based on the angle of the optical path formed around the cells as the light is scattered, thereby identifying the cells.

However, according to the above-described technique, when the cells are moved on a movement path of laser beam for the classification of target cells, the distribution of the components of the cells may be changed as the cells rotate, and as a result, the density of light collected by the photodetectors at different angles may be changed even in the same cell as the laser is irradiated in a single direction. Therefore, it has been noted that the cells cannot be accurately classified.

In addition, since a single laser beam is used, there is a problem in that blood cells, which may be identified as different cells despite the same shape, cannot be properly analyzed and classified.

In addition, since a unidirectional laser is used, there is a problem in that a very limited number of types (e.g., five types of WBC) of cells can be classified, and as a result, the efficiency of cell classification is greatly reduced.

DETAILED DESCRIPTION OF THE INVENTION

Technical Problem

Thus, an object of the present invention is to provide a light scattering cell classification technology which can accurately classify cells into various types and at the same time classify the cells with very high accuracy even if there is a difference in rotation and configuration of the cells.

Technical Solution

In order to achieve the above-described object, a cell analysis apparatus using a plurality of lasers, according to an embodiment of the present invention, includes: a plurality of laser generators installed around a movement path through which classification target cells are moved, and configured to irradiate a first laser beam, as at least one laser beam having at least one frequency, to a measurement point existing on the movement path; a plurality of photodetectors, installed around the one measurement point, and configured to collect a second laser beam, which is generated as the first laser beam irradiated from the laser generators is incident on cells and then refracted, reflected, transmitted, or fluoresced; and a cell analysis unit configured to classify classification target cells according to the second laser beam collected by the photodetectors.

Advantageous Effects

According to the present invention, second laser beams, which are irradiated at different angles or generated after first laser beams including different laser beams having different frequencies are irradiated to cells and then transmitted, refracted, reflected, or fluoresced by the cells, are collected by a plurality of photodetectors. Thus, the cells can be analyzed more accurately, so that the cells can be classified into various types.

In particular, even if the cells rotate on a movement path, it is possible to determine the three-dimensional second laser beam distribution by the laser beams irradiated at multiple angles. Further, since the first laser beams including different frequencies are irradiated from the same axis and the cells are analyzed based thereon, the cells can be classified with very high accuracy despite parameters, such as the rotation of the cells on the movement path, and different types of cells having the same shape can be more accurately determined.

MODE FOR CARRYING OUT THE INVENTION

Figure 1:
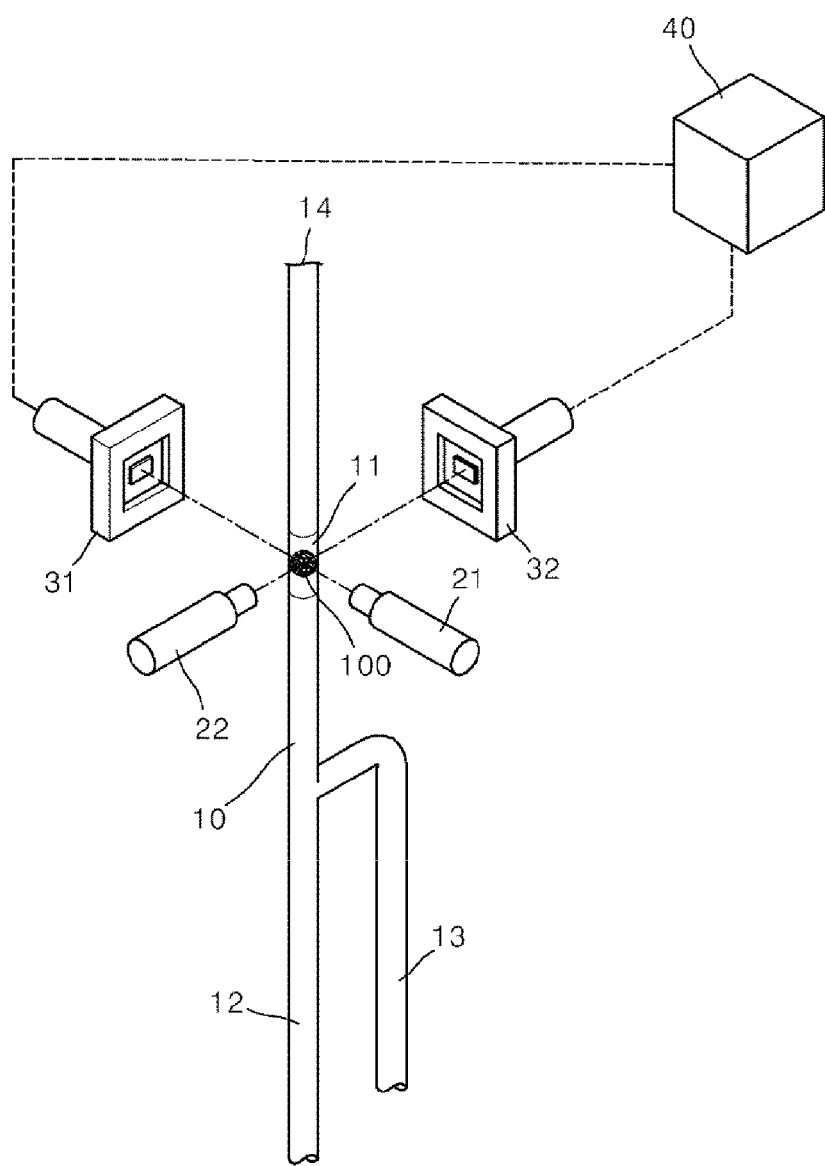
FIG. 1 is a perspective view illustrating the schematic configuration of a cell analysis apparatus using a plurality of lasers according to an embodiment of the present invention.

Hereinafter, a cell analysis apparatus that uses a plurality of lasers according to an embodiment of the present invention will be described with reference to the accompanying drawings.

It is natural that the following embodiments are described in detail in order to help the understanding of the present invention, and are not intended to limit the scope of the present invention. Accordingly, an equivalent invention, which executes the same function as the present invention, also falls within the scope of the present invention.

In addition, in adding reference numerals to the components in each of the drawings, it is noted that like components are denoted by like reference numerals even if the components are illustrated in different drawings. In the following description of the present description, a detailed description of known functions and configurations incorporated herein will be omitted when it is determined that the detailed description may make the subject matter of the present invention rather unclear.

Further, in describing components of the present invention, terms, such as "first," "second," "A," "B," "(a)," and "(b)" may be used. Such terms are used to distinguish the components from other components but the nature, order, and number of the components are not limited by the terms. In the case where it is described that a component is "connected," "coupled," or "joined" to another component, it should be understood that, although the former may be directly connected, coupled, or joined to the latter, a third component may be interposed between the components so as to be "connected," "coupled," or "joined" to each other.

FIG. 1 is a perspective view illustrating a schematic configuration of a cell analysis apparatus using a plurality of lasers according to an embodiment of the present invention.

Referring to FIG. 1, a cell analysis apparatus, which uses a plurality of lasers according to an embodiment of the present invention, includes a plurality of laser generators 21 and 22, a plurality of photodetectors 31 and 32, and a cell analysis unit 40.

The plurality of laser generators 21 and 22 are provided around a movement path 10 in which classification target cells 100 are moved so as to perform a function of irradiating a first laser beam as at least one laser beam having at least one intrinsic frequency (wavelength or color) to one measurement point 11 on the movement path 10.

The first laser beams emitted from the plurality of laser generators 21 and 22 have different intrinsic frequencies, and even if the first laser beams are converged at one measurement point 11 due to the characteristic of the laser beams, the first laser beams do not interfere with each other.

Meanwhile, in the first laser beams generated by the plurality of laser generators 21 and 22, laser beams having different frequencies may be included in one first laser beam. That is, laser beams having a plurality of frequencies may be included in the first laser beam that constitutes one same axis. As described above, due to the characteristics of the laser beams, even if laser beams having a plurality of frequencies are mixed and irradiated along the same axis, the laser beams do not interfere with each other.

Meanwhile, as illustrated in FIG. 1, different angles may be formed between the plurality of laser generators 21 and 22 based on the measurement point 11. That is, when the laser generators 21 and 22 are taken as a reference, a predetermined angle (e.g., 90 degrees) is formed on the basis of the measurement point 11, so that the first laser beams can be irradiated to the measurement point 11 at different angles.

The classification target cells 100 include all cells that need to be classified for determining symptoms, including normal cells (e.g., neutrophils, eosinophils, lymphocytes, lymphocytes, and monocytes) and abnormal cells (e.g., leukemia cells) as white blood cells, but are not limited thereto.

The classification target cells 100 are moved to an outlet 14 via a cell input path 13 and a fluid input path 12 for providing the moving force of the classification cell 100 through the measurement point 11. At this time, when the classification target cells 100 are located at the measurement point 11, the first laser beams emitted from the laser generators 21 and 22 are irradiated onto the classification target cells 100.

When the first laser beams emitted from the laser generators 21 and 22 are irradiated onto the classification target cells 100, the first laser beams are incident on the classification target cells 100, and are then transmitted, reflected, refracted, and fluoresced (a phenomenon in which the first laser beams are subjected to frequency modulation). As a result, other laser beams are generated, and the plurality of photodetectors 31 and 32 collect second laser beams, which are the laser beams generated in this way. For this purpose, as illustrated in FIG. 1, the plurality of photodetectors 31 and 32 may be installed around the measurement point 11, preferably at a position that corresponds to the direction in which the light generated from the laser generators 21 and 22 is scattered (transmitted, reflected, refracted, or fluoresced) by the classification target cells 100.

Figure 3:
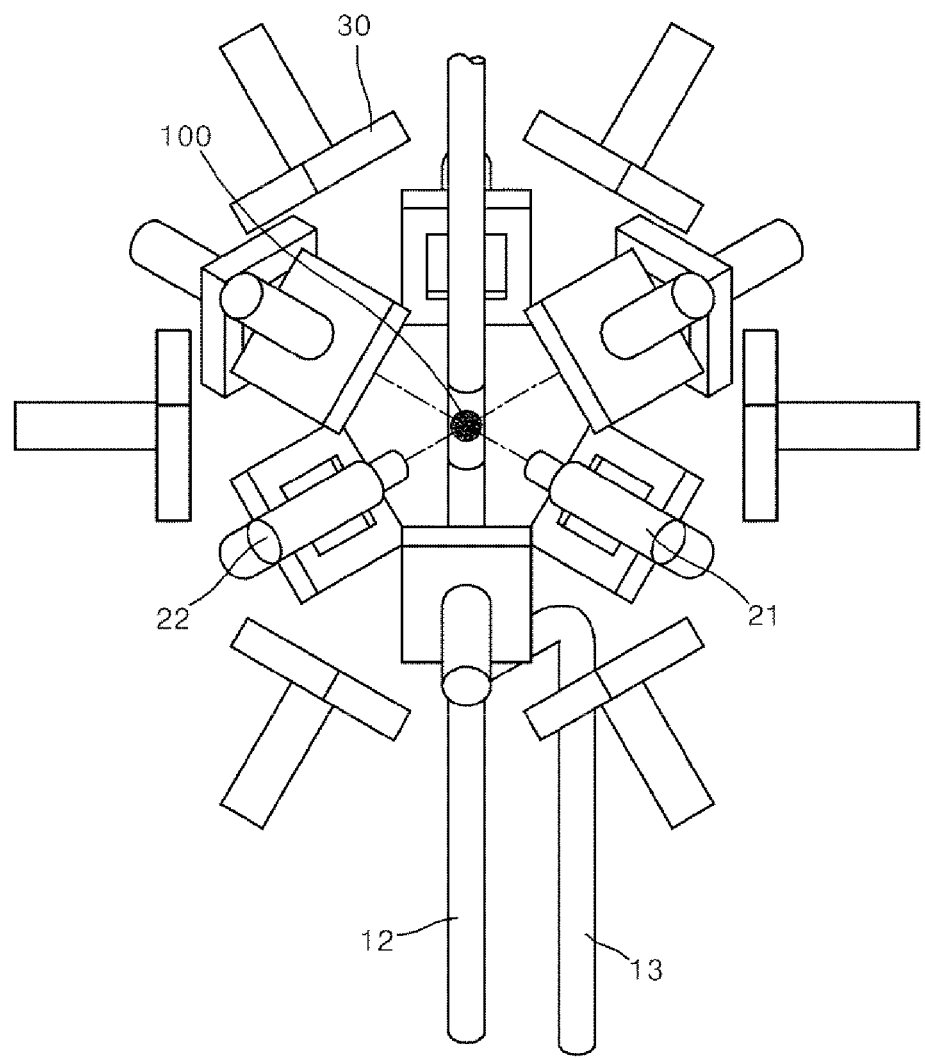
FIG. 3 is a perspective view illustrating a three-dimensional installation structure of photodetectors of a cell analysis apparatus that uses a plurality of lasers according to an embodiment of the present invention.

In the present invention, the second laser beams will be understood as a concept including all laser beams that are transmitted, reflected, refracted, or fluoresced by the classification target cells 100. In other words, the plurality of photodetectors 31 and 32 may also be provided at a position where they can collect reflected laser beams other than the positions illustrated in FIG. 1, and may be installed to collect fluoresced light. That is, in order to collect the second laser beams, at least some of the plurality of photodetectors 31 and 32 may be installed at a position where the reflected light reflected by the classification target cells 100 can be included in the second laser beams and collected at the time of collecting the second laser beams. Preferably, the plurality of photodetectors 31 and 32 may be arranged to surround the measuring point 11 as illustrated in FIG. 3 to be described later.

Meanwhile, as illustrated in FIG. 1, the plurality of photodetectors 31 and 32 may be provided around the one measurement point 11 so as to respectively collect different second laser beams that are generated from the first laser beams irradiated from the respective laser generators 21 and 22 in a manner in which the second laser beams of different frequencies or from different laser generators 21 and 22 are collected by the different photodetectors, respectively. That is, the photodetector 31 is installed to collect (detect) the second laser beam that is a laser beam generated as a laser beam irradiated from the laser generator 21 is scattered by the classification target cells 100, and the photodetector 32 is installed to collect (detect) the second laser beam that is a laser beam generated as a laser beam irradiated from the laser generator 22 is scattered by the classification target cells 100.

However, in another embodiment of the present invention, the second laser beams corresponding to two or more frequencies may be incident on some of the plurality of photodetectors 31 and 32 depending on the installation positions and angles of the laser generators 21 and 22, or all of the photodetectors 31 and 32 may be installed to collect the second laser beams corresponding to the laser beams having the plurality of frequencies in consideration of the characteristics of the second laser beams.

Accordingly, in another embodiment of the present invention, the plurality of photodetectors 31 and 32 may not be provided for each of the laser generators 21 and 22 as described above. Rather, the plurality of photodetectors 31 and 32 may collect the second laser beams of all frequencies, and may measure the frequencies of the collected second laser beams so as to sense frequency values. When the light amount information of the second laser beams collected by each of the plurality of photodetectors 31 and 32 is transmitted to the cell analysis unit 40 to be described later, the light amount information may be transmitted in a manner in which the light amount information includes frequency information of the second laser beams, measured as described above.

Meanwhile, the cell analysis unit 40 performs a function of classifying the classification target cells 100 according to the second laser beams collected by the photodetectors 31 and 32. Specifically, the process of classifying the classification target cells 100 by the cell analysis unit 40 is as follows.

According to the components such as nuclei that constitute cells, when the laser beams are irradiated to the cells, the laser beams are transmitted, refracted, reflected, or fluoresced based on the classification target cells 100. Using this effect, the distribution of the second laser beams, that is, the scattering angle and the light amount of each second laser beam, are collected and compared with previously stored reference information so as to classify the cells.

In the present invention, a plurality of first laser beams will be incident on the classification target cells 100 from the laser generators 21 and 22 at multiple angles. The incident beams will be transmitted, refracted, reflected, or fluoresced by the components of the classification target cells 100 as described above, so that the second laser beams will be generated. The scattering angle of the second laser beams may be formed in three-dimensions due to the characteristics of laser beam irradiation of multiple angles or multiple frequencies.

In order to use the above-described three-dimensional second laser beam information, reference second laser beam information may be stored in the cell analysis unit 40 as information obtained by sampling the light amount information of a plurality of three-dimensional second laser beams which was previously set when irradiating the first laser beam for each of the previously stored types of cells.

In consideration of the rotation of the classification target cells 100, the reference second laser beam information may be configured as information on a three-dimensional second laser beam distribution degree, rather than as the second laser beam information for each of three-dimensionally determined coordinates.

Also, the cell types matched for each piece of reference second laser beam information may include at least one normal cell type and at least one abnormal cell type for the purpose of cell classification. Taking white blood cells as an example, normal cells (e.g., neutrophils, eosinophils, adenocarcinomas, lymphocytes, monocytes) and abnormal cells (e.g., leukemia cells) may be, but not exclusively, included as respective classified types of cells.

On the basis of this, the cell analysis unit 40 calculates a light amount for each frequency of each laser beam using light amount information and frequency information as second laser beam information received and collected by each of the plurality of photodetectors 31 and 32 as described above, calculates three-dimensional second laser beam distribution information based on the calculated light amount, and then compares the information with the previously stored reference second laser beam information, whereby the classification target cells 100 are classified by matching them to a cell type corresponding to the reference second laser beam information that is determined as being matched as a result of the comparison among the pre-stored cell types.

In this way, as the second laser beam distribution can be determined by irradiating the laser beams at multiple angles, and the cells can be classified using the second laser beam distribution, the following effects can be obtained.

As described above, the conventional cell classification method classifies cells according to the second laser beams by irradiating only unidirectional beams. Accordingly, as the cells rotate on the movement path due to the characteristic thereof, the distribution of components of cells at the position where the beams are irradiated may be changed, and as a result, even for the same cell, the density of beams collected to the photodetectors at each angle, that is, the distribution of the second laser beams, may be varied. Accordingly, there is a problem in that the cells cannot be accurately classified. In addition, due to the unidirectional simplicity, it is only possible to classify cells into a very limited number of types.

Further, even in the case in which the cells have the same shape, the cells may be classified into different ones due to a difference in the components of the cells. However, in the case of analysis using a single-frequency laser beam, there is a problem in that different cells may not be distinguished.

However, as described above, when the first laser beams are irradiated even at two or more different angles or at coaxial axes at different frequencies and the two or three-dimensional distribution of the second laser beams obtained thereby is used as described above, it is possible to overcome the limit, caused due to the rotation of the cells, of the analysis of the second laser beam distribution, thereby enabling very accurate classification. In addition, it is possible to accurately classify cells having the same shape into different types of cells through the photo-reaction of cells for different frequencies. Further, by determining the distribution of the second laser beams at multiple angles, the cells can be determined very accurately, so that the cells can be classified into a greater variety of types.

Figure 2:
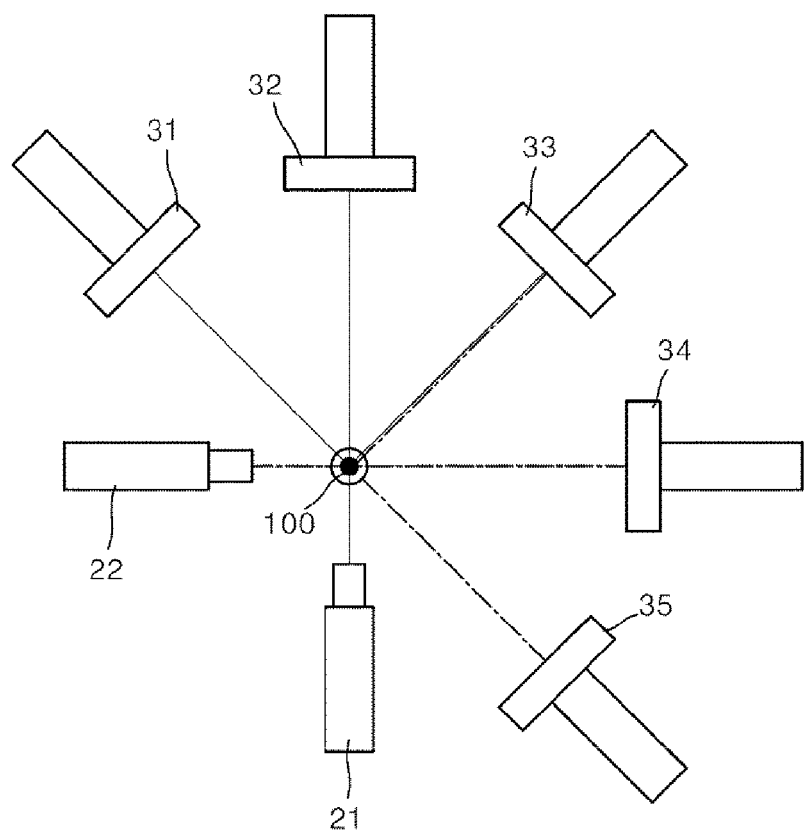
FIG. 2 is a plan view illustrating an installation structure of photodetectors of a cell analysis apparatus that uses a plurality of lasers according to an embodiment of the present invention.

FIG. 2 is a plan view illustrating an installation structure of photodetectors of a cell analysis apparatus that uses a plurality of lasers according to an embodiment of the present invention. In the following description, a description overlapping with the description made above with reference to FIG. 1 will be omitted.

Referring to FIG. 2, two laser generators 21 and 22 are provided to form, for example, right angles with respect to the classification target cells 100. FIGS. 1 to 3 of the present invention illustrate that two laser generators 21 and 22 are installed to form right angles with each other. However, this is merely an example for describing the present invention, and it is natural that three or more laser generators may be installed to form various angles.

As the first laser beams emitted from the corresponding laser generators 21 and 22 are incident on the classification target cells 100, second laser beams are generated, as indicated by the dotted lines and dashed lines, respectively. Of course, as described above, the angle of the second laser beams is not limited to that illustrated in FIG. 2, but may also be formed to be a reflected angle. It can be understood that FIG. 2 illustrates the second laser beams at limited angles merely for describing the above-mentioned functions.

Unlike FIG. 1, in FIG. 2, it can be seen that in order to more closely measure the distribution of the above-mentioned second laser beams, a plurality of photodetectors 31 to 35 are installed in an arrangement that surrounds the classification target cells 100.

The plurality of photodetectors 31 to 35 may be provided so as to correspond to the respective laser generators 21 and 22, as described in the description of FIG. 1. For example, it can be seen that the photodetectors 31 and 32 and the photodetectors 34 and 35 are illustrated to irradiate only the second laser beam generated by the first laser beam irradiated from the laser generator 21 and the second laser beam generated by the first laser beam irradiated from the laser generator 22, respectively.

Meanwhile, as mentioned above, for example, the photodetector 33 can collect the second laser beam generated by all of the laser generators 21 and 22. The functions of the photodetectors have been described with reference to FIG. 1.

As described above, the plurality of photodetectors 31 to 35 are disposed to surround the position where the measurement point, that is, the classification target cell 100, is irradiated with the first laser beams, so that a greater variety of second laser beam distributions can be measured.

Meanwhile, FIG. 3 is a perspective view illustrating a three-dimensional installation structure of photodetectors of a cell analysis apparatus that uses a plurality of lasers according to an embodiment of the present invention. In the following description of FIG. 3, a description overlapping with the descriptions made above with reference to FIGS. 1 and 2 will be omitted.

Referring to FIG. 3, which is based on FIG. 2, beams emitted from the plurality of laser generators 21 and 22 are transmitted, reflected, refracted, or fluoresced not only in two dimensions, but also in three dimensions. That is, although FIG. 2 illustrates a configuration for collecting second laser beams that form a two-dimensional angle, as can be seen from FIG. 3, a plurality of photodetectors 30 may be installed in three-dimensional regions around the measurement point at which the laser beams are incident while the classification target cells 100 are moved through the fluid input path 12 and the cell input path 13, which have been described above with reference to FIG. 1, so that the photodetectors three-dimensionally surround the corresponding measurement point.

At this time, as illustrated in FIG. 3, since the photodetectors 30 are installed in order to collect the above-mentioned three-dimensional second laser beams, it is possible to more accurately measure the second laser beam distribution in three dimensions, so that the function of the present invention can be carried out.

Figure 4:
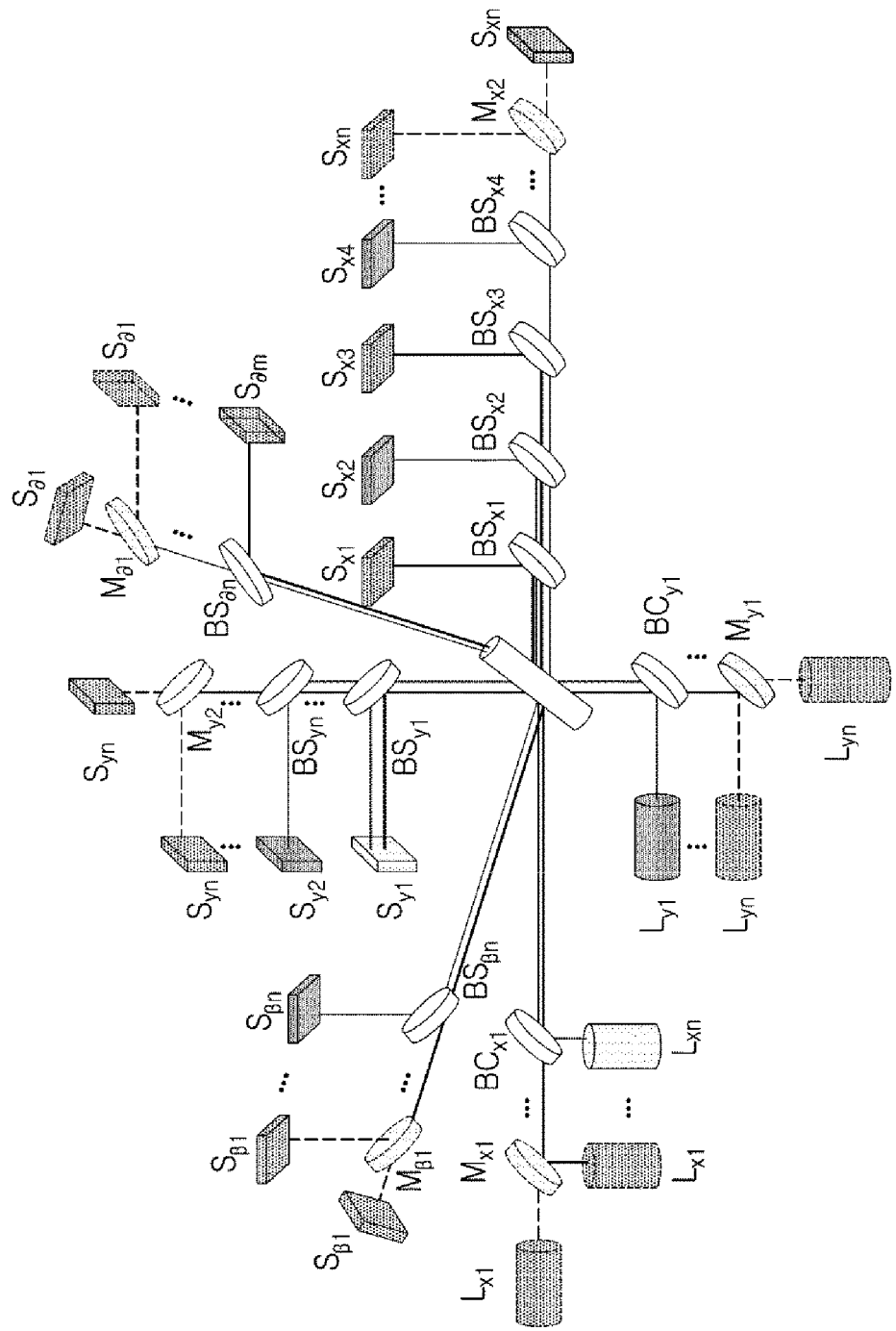
FIG. 4 is a view for describing a specific configuration of laser generators and photodetectors for illustrating a specific example of irradiating first laser beams at coaxial and different angles and collecting second laser beams generated by the cells, according to an embodiment of the present invention.

FIG. 4 is a view for describing a specific configuration of laser generators and photodetectors for illustrating a specific example of irradiating first laser beams at coaxial and different angles and collecting second laser beams generated by the cells, according to an embodiment of the present invention. Specifically, FIG. 4 is a view for describing an example of irradiating first laser beams of multiple frequencies at multiple angles and at the same axis, and collecting the second laser beams by a plurality of photodetectors at different positions.

First, in FIG. 4, components indicated by letters starting with a capital "L" mean all components that can generate a first laser beam, such as a laser diode and a laser irradiation device. Meanwhile, components indicated by letters starting with a capital "S" mean all components that can function as a photodetector, such as a photo diode and a photomultiplier (PMT). Components indicated by letters starting with a capital "M" mean mirrors, components indicated by letters starting with capitals "BC" mean beam combiners, and components indicated by letters starting with capitals "BS" mean beam splitters.

As illustrated in FIG. 4, laser beams are generated from a plurality of light sources $L_{x1}$ to $L_{xn}$ in a single-axis laser generator, and the generated laser beams are mixed by mirrors $M_{x1}$ and beam combiners $BC_{x1}$ to be irradiated to classification target cells 100 as first laser beams.

Meanwhile, laser beams are also generated from a plurality of light sources $L_{y1}$ to $L_{yn}$ in the laser generator of the other axis, and the generated laser beams are mixed by mirrors $m_{y1}$ and beam combiners $BC_{y1}$ to be irradiated, as first laser beams, to the classification target cells 100 at an angle different from that of the above-mentioned single-axis laser generator.

When the first laser beams including laser beams having at least one frequency are irradiated to the classification target cells 100 at different angles as described above, the first laser beams are transmitted, reflected, refracted, or fluoresced by the classification target cells 100, thereby generating second laser beams.

Referring to the example of FIG. 4, a second laser beam generated by the transmission of a beam $L_{x1}$ is collected at $S_{x3}$, a second laser beam generated by the transmission of a beam $L_{xn}$ is collected at $S_{x2}$, a second laser beam generated by the transmission of a beam $L_{y1}$ is collected at $S_{y2}$, and a second laser beam generated by the transmission of a beam $L_{yn}$ is collected at $S_{yn}$.

Meanwhile, refracted and reflected beams may be collected as follows. Referring to the example of FIG. 4, second laser beams generated by the refraction or reflection of the beam $L_{x1}$ are collected at $S_{\beta1}$ and $S_{\ni n}$, respectively. A second laser beam generated by the refraction or reflection of the beam $L_{xn}$ is collected in $S_{y1}$. A second laser beam generated by the refraction or reflection of the beam $L_{y1}$ is collected at $S_{x4}$, and a second laser beam generated by the refraction or reflection of the light $L_{yn}$ is collected at $S_{xn}$.

Meanwhile, fluoresced beams may also be collected. When a beam is fluoresced, the frequency thereof is modulated so that the color of the beam may be changed, which is represented as beams, which are collected at $S_{\beta n}$, $S_{\ni 1}$, $S_{\ni n}$, and $S_{x1}$, respectively, as can be seen from FIG. 4.

Each collected beam may be classified and collected at every frequency by the mirrors $M_{\beta1}$, $M_{y2}$, $M_{\ni 1}$, and $M_{x2}$ and optical splitters $BS_{\beta n}$, $BS_{y1}$ to $BS_{yn}$, $BS\ni_n$, and $BS_{x1}$ to $BS_{x4}$.

Figure 5:
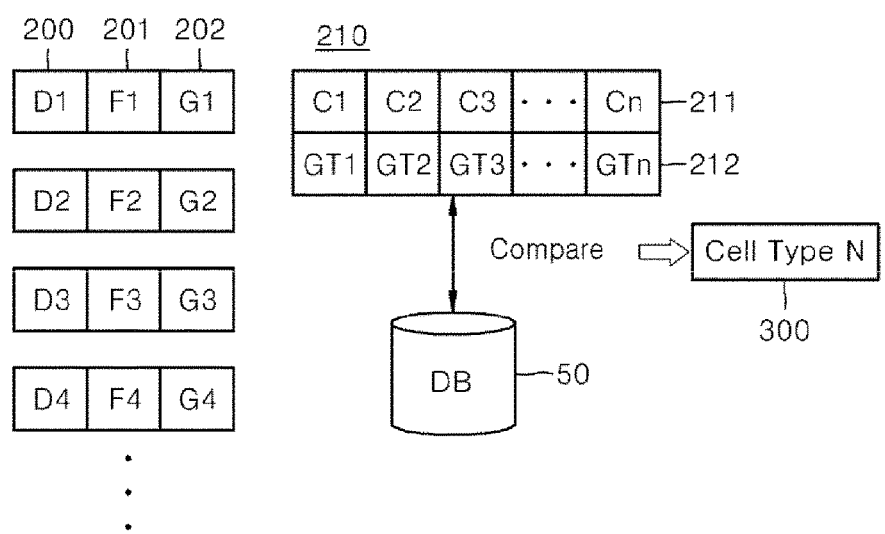
FIG. 5 is a view for describing a flow in which cells are classified according to the implementation of an embodiment of the present invention.

FIG. 5 is a view for describing a flow in which cells are classified according to the implementation of an embodiment of the present invention.

Referring to FIG. 5, information on the collection of the second laser beams transmitted to the cell analysis unit, that is, information on the light amount of the second laser beams (including G1 to G4) collected at each of the photodetectors (including D1 to D4) may include identification information 200 of respective photodetectors D1 to D4, frequency information 201 of beams collected by the photodetectors (including F1 to F4), and light amount information 202.

The cell analysis unit, which receives the above-mentioned information, will calculate three-dimensional second laser beam distribution information 210, which may include, for example, cumulative second laser beam density 212 (GT1 to GTn) at each of measurement points 211 (C1 to Cn) set in three dimensions.

The three-dimensional second laser beam distribution information is compared with the reference second laser beam information stored in a database 50, and cell type information 300 matching the reference second laser beam information is classified as a classification target cell type.

Even if it has been described that all of components, which constitutes an embodiment, are integrally coupled or functionally coupled, it should be understood that the present invention is not necessarily limited to such an embodiment. That is, within the scope of the object of the present invention, one or more of the components may be selectively coupled to operate. In addition, all of the components may be individually implemented as a single piece of independent hardware. However, some or all of the components may be selectively combined and implemented as a computer program having a program module that performs some or all of the functions combined in a single piece or multiple pieces of hardware. Codes and code segments, which configure a computer program, may be easily conceived by a person ordinarily skilled in the art. Such a computer program may be stored in a computer-readable storage medium, and read and executed by a computer, thereby implementing an embodiment of the present invention. The storage medium of the computer program may include a magnetic recording medium, an optical recording medium, and the like.

The terms "including," "configuring," and "having," as used in the foregoing description mean that another component may be included unless specifically described otherwise, and should be interpreted to mean that other components may be further included, rather than being excluded. All terms, including technical and scientific terms, have the same meanings as those commonly understood by a person ordinarily skilled in the art to which the present invention belongs, unless otherwise defined. Commonly used terms, such as predefined terms, should be interpreted to be consistent with the contextual meaning of the relevant art, and are not to be construed as an ideal or overly formal sense unless expressly defined.

The forgoing description merely illustratively describes the technical idea of the present invention, and various changes and modifications may be made by a person ordinarily skilled in the art without departing from the essential characteristics of the present invention. Therefore, the embodiments disclosed herein are not intended to limit the scope of the present invention, but to describe the technical idea of the present invention, and the scope of the technical idea of the present invention is not limited by the embodiments. The protection scope of the present invention should be interpreted based on the following claims, and all technical ideas within the scope of equivalents thereof should be construed as being included in the scope of the present invention.

The invention claimed is:

1. A cell analysis apparatus using a plurality of lasers, the cell analysis apparatus comprising:
    a plurality of laser generators installed around a flow conduit through which classification target cells are moved, the plurality of laser generators configured to irradiate first laser beams at a plurality of different angles and having a plurality of different frequencies directed to a measurement point along the flow conduit, the first laser beams irradiated from the laser generators are incident on the cells and are refracted, reflected, transmitted, or fluoresced by the target cells in three dimensions, wherein the plurality of laser generators are arranged in a common plane and include a first group of laser generators directing multiple first laser beams along a first axis and a second group of laser generators directing multiple first laser beams along a second axis;
    a plurality of photodetectors directed at various different angles towards the measurement point of the flow conduit to which each one of the plurality of laser generators is directed, the plurality of photo detectors include a first group of photodetectors arranged in the common plane with the plurality of laser generators, a second group of photodetectors arranged above the common plane, and a third group of photodetectors arranged below the common plane to collect second laser beams of different frequencies and angles that have been refracted, reflected, transmitted, or fluoresced by the target cells in the common plane, above the common plane, and below the common plane; and
    a cell analysis unit that classifies the classification target cells according to the second laser beams collected by the photodetectors.

2. The cell analysis apparatus of claim 1, wherein the plurality of photodetectors are arranged such that the measurement point is centered amongst the plurality of photodetectors.

3. The cell analysis apparatus of claim 1, wherein the plurality of photodetectors measure frequencies of the collected second laser beams, the frequencies are transmitted to the cell analysis unit.

4. The cell analysis apparatus of claim 1, wherein the cell analysis unit stores reference parameters of second laser beam information for each one of a plurality of different reference cell types, and
    wherein the cell analysis unit compares parameters of the collected second laser beams with the reference parameters and based on the comparison classifies each one of the classification target cells as one of the plurality of different reference cell types, and wherein the reference cell types include at least one normal cell type and at least one abnormal cell type.

5. The cell analysis apparatus of claim 1, wherein at least some of the plurality of laser generators are provided such that the plurality of laser beams are irradiated as the first laser beams by coaxially irradiating a plurality of laser beams having a plurality of frequencies.

* * * * *